United States Patent [19]

Kikuchi

[11] Patent Number: 5,045,934
[45] Date of Patent: Sep. 3, 1991

[54] ELECTRONIC ENDOSCOPE APPARATUS CAPABLE OF INDICATING OVER-EXPOSURE AREA ON FUNCTIONAL IMAGE

[75] Inventor: Katsuya Kikuchi, Tochigi, Japan
[73] Assignee: Kabushiki Kaisha Toshiba, Kawasaki, Japan
[21] Appl. No.: 489,051
[22] Filed: Mar. 7, 1990
[30] Foreign Application Priority Data
Apr. 12, 1989 [JP] Japan ............................. 1-90569
[51] Int. Cl.⁵ .................. H04N 7/18; A61B 1/04; A61B 1/06
[52] U.S. Cl. ............................. 358/98; 128/6
[58] Field of Search .......................... 358/98; 128/6

[56] References Cited

U.S. PATENT DOCUMENTS 4,884,134 11/1989 Tsuji et al. .......................... 358/98
4,914,512 4/1990 Sekiguchi ........................ 128/6 X Primary Examiner—Kenneth A. Wieder
Assistant Examiner—Glenn W. Brown
Attorney, Agent, or Firm—Foley & Lardner

[57] ABSTRACT

In an electronic endoscope apparatus, a region having an over exposure level within a functional image of a biological body under medical examination is detected and displayed, such as a hemoglobin concentration distribution image superimposed thereon. The electronic endoscope apparatus includes a unit for processing a functional information image signal so as to detect a region having an exposure level exceeding over an allowable maximum exposure level, and for superimposing the region having the over-exposure level on the functional information image signal; and, a monitor for displaying both a functional information image and the over-exposure region superimposed thereon based upon the functional information image signal and the detected over-exposure region.

7 Claims, 3 Drawing Sheets

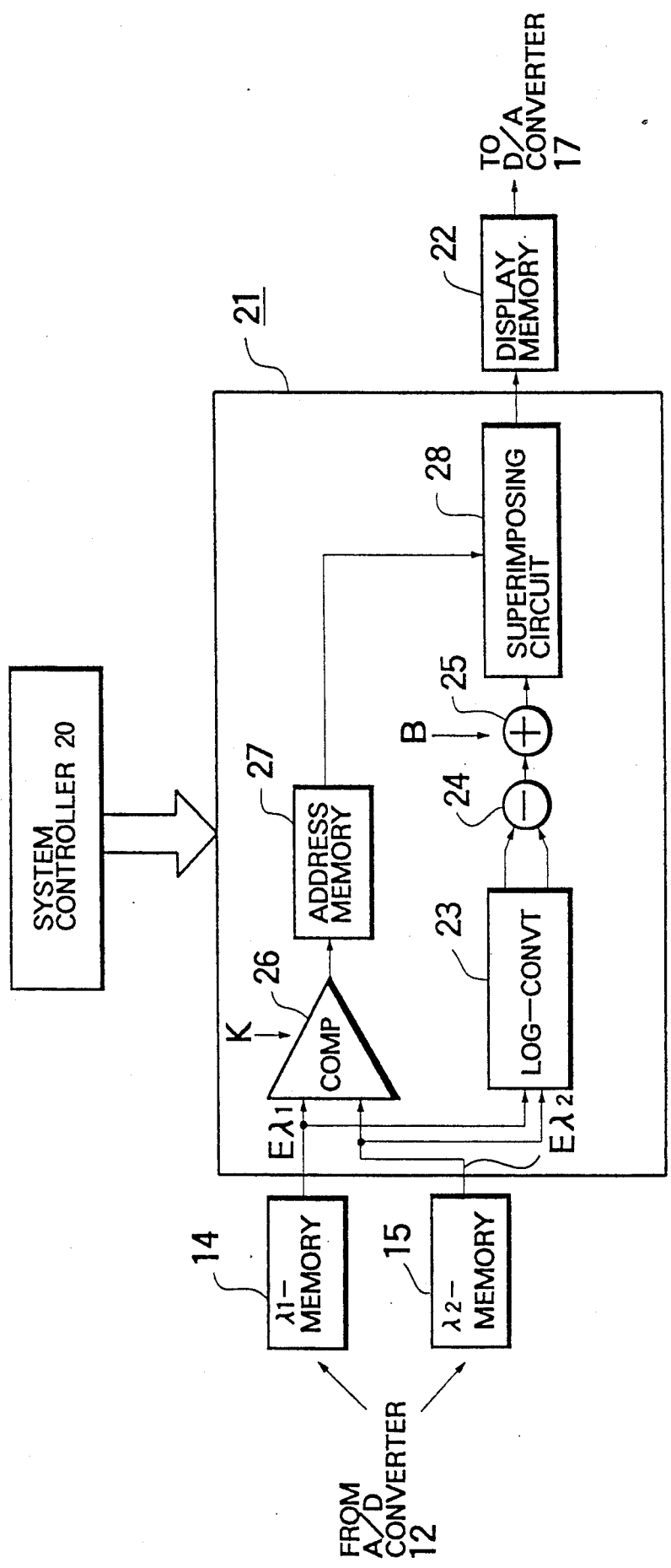

ELECTRONIC ENDOSCOPE APPARATUS CAPABLE OF INDICATING OVER-EXPOSURE AREA ON FUNCTIONAL IMAGE

BACKGROUND OF THE INVENTION

1. Field of the Invention

The present invention generally relates to an electronic endoscope apparatus, and more specifically, to an electronic endoscope apparatus capable of measuring functional information data such as hemoglobin concentration and oxygen saturation hemoglobin, and of indicating this information on a functional image.

2. Description of the Related Art

Recently, research have been directed to relationships between blood flow conditions of submucosa of an organ, e.g., a stomach, and diseases such as gastric ulcer, and many attempts have been made to image functional information such as hemoglobin concentration and oxygen saturation of hemoglobin for diagnostic purposes.

In one conventional electronic endoscope apparatus, when a hemoglobin-concentration distribution image of a biological body is acquired, for instance, an interior portion of a stomach is photographed under lighting conditions of transmission wavelengths of 569 nm (nanometers) and 650 nm, and then a difference is calculated between absorbance values of the two filtered images.

In accordance with the above-described conventional electronic endoscope apparatus, the following difficulties may occur. That is, when the exposure amount of the lighting operation exceeds a certain allowable value, due to movements of the stomach and photographing conditions, either acquired image data, or both image data contain a light intensity over this allowable limit. Namely, even when, for example, the subject (e.g., an interior portion of a stomach) can now be photographed under the optimum exposure value, if this subject will approach the CCD (imaging sensor) of the endoscope apparatus, the subject might be photographed in an over-exposure condition. If the subject is, for instance, the stomach of a biological body, the stomach continuously moves during the endoscopic observation. As a consequence, such an over exposure phenomenon may surely occur. When such a difficulty may be introduced, the calculated difference between the absorbance values of two filtered images may contain an incorrect value, which may result in erroneous functional information of the stomach. Thus, the diagnostic data quality may be deteriorated. Moreover, there is a further problem that no means for recognizing that such incorrect data is employed in the conventional electronic endoscope apparatus. Such electronic endoscope apparatuses are known from, for instance, Japanese KOKAI (Disclosure) patent application No. 58-65138 in 1983.

The present invention has been made in an attempt to solve the above-described problems, and therefore has as an object an electronic endoscope apparatus capable of recognizing to an endoscope operator that an over-exposure region is contained in a functional information image.

SUMMARY OF THE INVENTION

The above-described object of the present invention may be achieved by providing an electronic endoscope apparatus (100) comprising:

a light source (2) for illuminating an interior portion of a biological body (30) under medical examination;

filter means (9) selectively interposed between the light source (2) and illuminated interior portion of the biological body for filtering out light having a preselected transmission wavelength, and for projecting said filtered light to the interior portion thereof;

image sensor means (4) for imaging the illuminated interior portion by receiving the filtered light therefrom to thereby produce a functional information image signal;

means (21) for processing said functional information image signal so as to detect a region having an exposure level exceeding over an allowable maximum exposure level, and for superimposing said region having the over-exposure level on said functional information image signal; and, means (19) for displaying both a functional information image and said over-exposure region superimposed thereon based upon said functional information image signal and said detected over-exposure region.

BRIEF DESCRIPTION OF THE DRAWINGS

The present invention may be best understood with reference to the following detailed description in conjunction with the accompanying drawings, in which:

FIG. 3 is a schematic block diagram of an internal circuit of the calculation unit 21 shown in FIG. 1; and, FIG. 4 illustrates an over-exposure region superimposed on a hemoglobin concentration distribution image.

DETAILED DESCRIPTION OF THE PREFERRED EMBODIMENTS

Basic Idea

Before describing various types of electronic endoscope apparatuses according to the preferred embodiments of the present invention, a basic idea of the invention will now be summarized.

In an electronic endoscope apparatus capable of imaging functional information such as a hemoglobin concentration distribution of a stomach submucosa, there are employed an over-exposure region detecting means for detecting an over-exposure region having a certain exposure level exceeding an allowable maximum exposure level from each of functional image data which have been acquired under conditions that an interior portion of the stomach is photographed, while utilizing interference filters with different light transmission wavelengths; and, display control means for controlling a display of the over-exposure region on the functional image. For instance, the over-exposure region is superimposed on the displayed functional image.

In accordance with the electronic endoscope apparatus with the above-described arrangements, the over-exposure region of the photographed stomach is indicated, or superimposed on the functional image thereof. As a consequence, an operator can readily recognize the existence of such an over-exposure region for reflecting incorrect functional information data from the displayed overall functional information image.

Arrangement of Electronic Endoscope Apparatus

Figure 1:
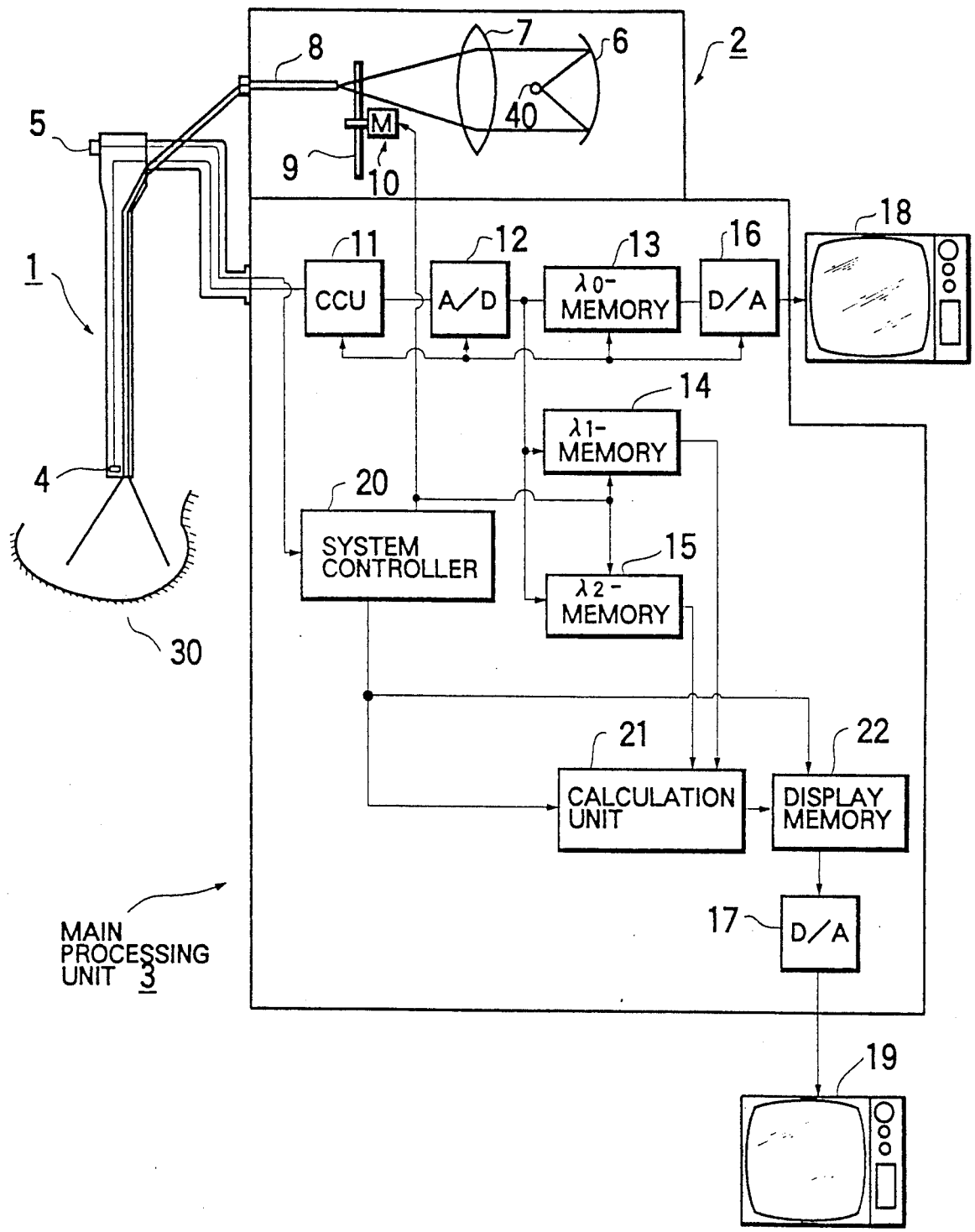
FIG. 1 is a schematic block diagram of an electronic endoscope apparatus according to a first preferred embodiment of the invention.

In FIG. 1, there is shown an electronic endoscope apparatus 100 according to a preferred embodiment, to which the above-described basic idea of the present invention has been applied.

Briefly speaking, the endoscope apparatus 100 is mainly constructed of an endoscopic scope unit 1, a light source unit 2, and a main processing unit 3.

The endoscopic scope unit 1 includes a CCD (charge-coupled device) imaging element 4 positioned at a distal end of the scope, and a hemoglobin image acquisition button 5 positioned at a grip portion thereof.

The light source unit 2 is constructed of a xenon lamp 40 and a reflector 6, a collecting lens 7; a light guide 8 conducts light to the distal end of the scope; filter disk 9 equipped with narrow transmission bandwidth filters (i.e. interference filters); and a stepping motor 10. The light guide 8 is positioned within an optical path along which the collecting lens 7 and light source 6 are arranged.

The main processing unit 3 is constructed of a camera control unit (CCU) 11, an analog-to-digital converter 12, image memories 13, 14 and 15, digital-to-analog converters 16 and 17, TV monitors 18 and 19, a system controller 20, a calculation unit 21, and a display memory 22.

Figure 2:
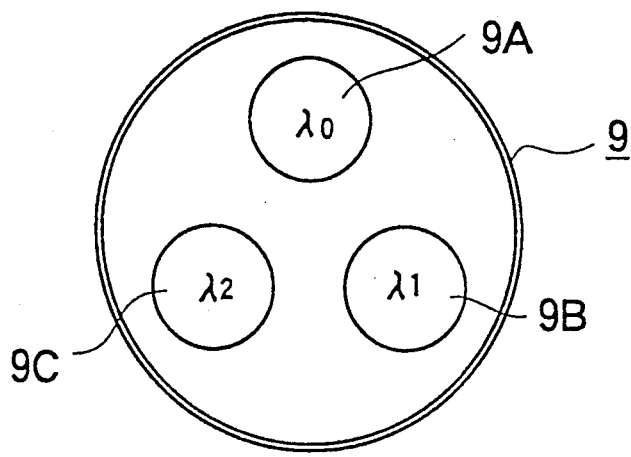
FIG. 2 schematically illustrates a filter disk employing interference filters employed in the endoscope apparatus shown in FIG. 1.

Precisely speaking, the filter disk 9 employed in the light source unit 2 is so constructed that, as represented in FIG. 2, an open filter 9A and two different interference filters 9B and 9C are equidistantly arranged along a peripheral direction of this filter disk 9. The first interference filter 9B has a central transmission wavelength of 569 nm ($\lambda_1$), whereas the second interference filter 9C has a central transmission wavelength of 650 nm ($\lambda_2$). These interference filters 9B and 9C are used to acquire functional image data of the subject (i.e., biological body) 30 under medical examination, whereas the open filter 9A is utilized so as to obtain a normal observation image thereof (will be discussed later).

The system controller 20 controls the overall system, for instance, to drive the stepping motor 10 of the light source unit 2, to write/read data into/from the image memories 14 and 15, and to control the calculation unit 21 and display memory 22.

Calculation Unit

Various functions of the calculation unit 21 constitute the major feature of the present invention, and calculate the distribution of hemoglobin concentrations. Accordingly, this calculation unit 21 functions as an over-exposure region detecting means and a superimposed image display controlling means.

An algorithm to calculate the hemoglobin concentration distribution can be expressed based upon the following equation (1), if a hemoglobin index is denoted by "IHb":

$$IHb = 200 \cdot C$$

$$C = \log E\lambda_2 - \log E\lambda_1 - B \quad (1)$$

where "$E\lambda_1$" represents an output value derived from the camera control unit 11 under the condition that the subject 30 is photographed under a lighting condition with the interference filter 9B having the transmission wavelength of 569 nm (nanometers), and "$E\lambda_2$" indicates another output value derived therefrom under the lighting condition with the interference filter 9C having the transmission wavelength of 650 nm, and "B" denotes a constant as a correction coefficient.

In FIG. 3, there is shown a detailed circuit of the calculation unit 21. This calculation unit 21 includes a first combination of a logarithmic converting circuit 23, a subtracting circuit 24 and an adding circuit 25 to calculate the hemoglobin concentration distribution data; a second combination of a comparator 26 and an address memory 27 to detect the above-described over-exposure region from the acquired functional image data; and a superimposing circuit 28 for superimposing the over-exposure region on the functional image of the above-explained hemoglobin concentration distribution.

Entire Operation

Referring now to FIGS. 1 to 3, an entire endoscopic operation of the electronic endoscope apparatus 100 according to the first preferred embodiment will be described.

When the interior portion of the subject 30, e.g., a stomach of a biological body is observed, the open filter 9A of the filter disk 9 is selected by the stepping motor 10 under control of the system controller 20 so as to be inserted into the optical path of the light source unit 2. An image signal derived from the CCD imaging element 4 is converted into a corresponding video signal in the camera control unit 11. This video signal is then A/D-converted into a digital video signal by an analog-to-digital converter 12. The digital video data (signals) are sequentially written into the image memory ($\lambda_{SIS}$-memory) 13 and also read out therefrom under the control of the system controller 20. The read video data are D/A-converted into corresponding analog video signals by the D/A converter 16. This analog video signal is supplied to a first TV monitor 18, whereby the imaged interior portion of the subject 30 is displayed thereon in real time.

Over-Exposure Region Indicated on Functional Image

When the button 5 for acquiring the hemoglobin concentration distribution image is depressed, the filter disk 9 is rotated by the stepping motor 10 under control of the system controller 20 as to successively select the interference filters 9B ($\lambda_1$) and 9C ($\lambda_2$). The selected interference filter 9B or 9C is inserted into the optical path of the light source unit 2, so that the interior portion of the subject 30 is photographed from lighting with the selected interference filter. In synchronization with this photographing operation, data read/write operations of the second and third image memories 14 ($\lambda_1$-memory) and 15 ($\lambda_2$-memory) are carried out under the control of the system controller 20. Thus, each of the filtered images $\lambda_1$, $\lambda_2$ is stored into the corresponding image memories 14 and 15 under the control of the system controller 20. At this time, the image of the subject 30 which has been acquired just before the button 5 for acquiring the hemoglobin concentration distributed image is depressed, is being displayed on the first TV monitor 18 in a freeze mode. Then, when the above-described filtered image has been acquired, the normal observation image of the subject 30 is simultaneously again displayed on the first TV monitor 18 in real time.

In accordance with the preferred embodiment, the above-described equation (1) for calculating the hemoglobin distribution image data is calculated in the calculation unit 21 shown in FIG. 3, and the over-exposure region may be superimposed on the functional image (i.e., hemoglobin distribution image). In the calculation unit 21 represented in FIG. 3, the filtered image data "E$\lambda_1$" and "E$\lambda_2$" supplied from the corresponding image memories 14 and 15 are logarithm-converted in the logarithm converting circuit 23 to obtain image data "logE$\lambda_1$" and "logE$\lambda_2$". The converted image data, "logE$\lambda_1$" in the subtracting circuit 24 is applied to adding circuit 25. The resultant data is added to the above-described constant "B" in the adding circuit 25. The data image sum is fed to superimposing circuit 28.

On the other hand, the comparator 26 compares one image data "E$\lambda_1$" with a predetermined constant value "K" so as to judge whether or not a pixel value of the image data "E$\lambda_1$" exceeds this constant value "K". This pixel value is proportional to an exposure amount. This constant value "K" is determined as, for instance, 80% of a full-scale value. In other words, a judgement is made whether or not the pixel value of the image data "E$\lambda_1$" becomes the over-exposure level. If the judged pixel value exceeds the constant value "K", the address of this pixel is stored in the address memory 27. Similarly, the comparator 26 compares the other image data "E$\lambda_1$" with this constant value "K" in order to judge whether or not a pixel value of this image data "E$\lambda_2$" exceeds over the constant value "K". Then, an address of the exceeding pixel is stored in the address memory 27. As a result, all of the address data on the pixels exceeding over the constant value "K" are stored in the address memory 27. These address data are supplied to the superimposing circuit 28 so that the over-exposure region represented by the address data is superimposed on the functional image, e.g., the hemoglobin concentration distribution image displayed on the second TV monitor 19 (see FIG. 4).

Figure 4:
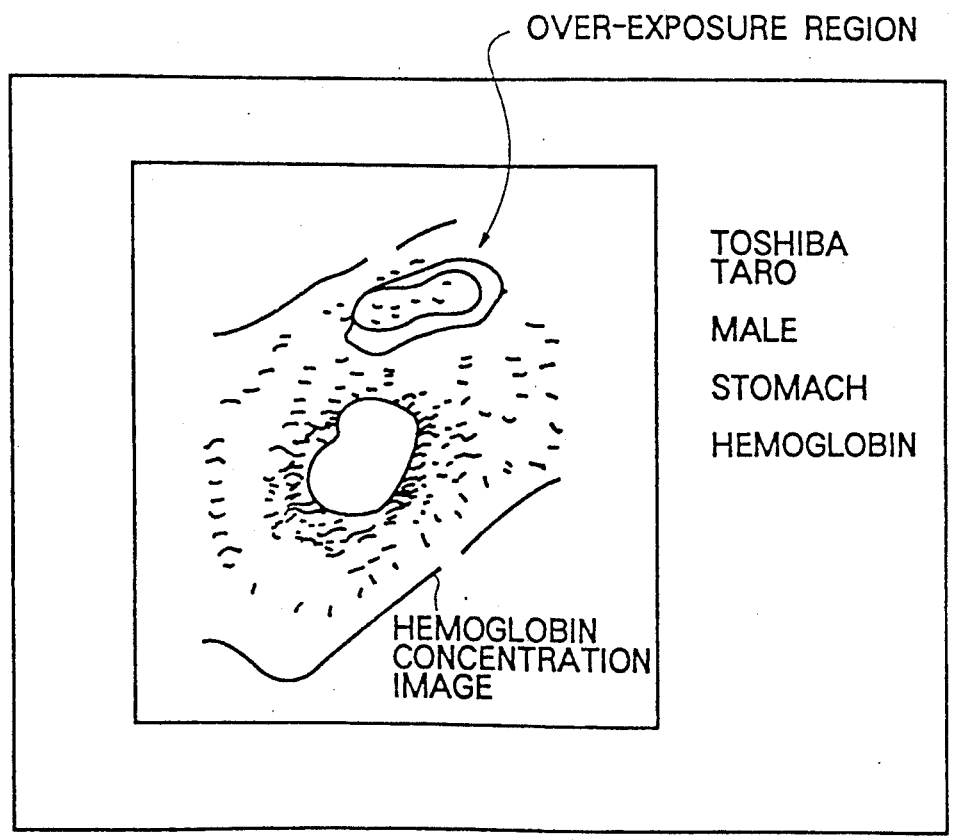

As represented in FIG. 4, the hemoglobin concentration distribution of the functional image is displayed in such a manner that the amount of the hemoglobin concentration is intensity-modulated, whereas the over-exposure region is displayed in red, for instance, on the second TV monitor 19.

It should be understood that although the calculation by the calculation unit 21 is carried out for the over-exposure data on the hemoglobin concentration in the above-described preferred embodiment, other functional information such as oxygen saturation of hemoglobin may be readily processed in the similar manner according to the present invention.

While the present invention has been described in detail, the electronic endoscope apparatus according to the present invention can process the functional information of the subject under medical examination, and also can detect the over-exposure region from the functional image data so as to superimpose such an over-exposure region on the functional image. As a consequence, it can be avoided such a risk that a diagnosis is made the functional image containing the incorrect functional information data caused by the over-exposure region.

What is claimed is:

1. An electronic endoscope apparatus comprising:

a light source for illuminating an interior portion of a biological body under medical examination;

filter means selectively interposed between the light source and illuminated interior portion of the biological body for filtering out light having a preselected transmission wavelength, and for projecting said filtered light to the interior portion thereof;

image sensor means for imaging the illuminated interior portion by receiving the filtered light therefrom to thereby produce a functional information image signal;

means for processing said functional information image signal so as to detect a region having an exposure level exceeding over an allowable maximum exposure level, and for superimposing said region having the over-exposure level on said functional information image signal; and, means for displaying both a functional information image of the biological body and said over-exposure region superimposed thereon based upon said functional information image signal and said over-exposure region.

2. An electronic endoscope apparatus as claimed in claim 1, wherein said processing/superimposing means includes:

a calculation unit for calculating functional information data from said functional information image signal;

a detection unit for detecting said over-exposure region from said functional information image data; and, a superimposing unit for superimposing said over-exposure region on said functional image.

3. An electronic endoscope apparatus as claimed in claim 2, wherein said calculation unit includes:

a logarithm converting unit for converting said functional information data to obtain logarith-converted functional information data;

a subtracting circuit for performing subtraction between the logarithm-converted functional information data sequentially obtained under the different filtered lighting conditions; and, an adding circuit for adding a first constant value to a result of said subtracting circuit so as to thereby produce said functional information image.

4. An electronic endoscope apparatus as claimed in claim 2, wherein said detecting unit includes a comparator for comparing said functional information data with a second constant value so as to detect whether or not said exposure level of the area exceeds over said allowable maximum exposure level, whereby said over-exposure region is detected.

5. An electronic endoscope apparatus as claimed in claim 2, wherein said superimposing unit includes:

an address memory for storing said over-exposure region; and, a superimposing circuit for superimposing said over-exposure region on said functional information image signal based upon said stored address.

6. An electronic endoscope apparatus as claimed in claim 1, wherein said filter means includes a disk and at least a first interference filter having a first transmission wavelength and a second interference filter having a second transmission wavelength.

7. An electronic endoscope apparatus as claimed in claim 1, wherein said functional image represents one of hemoglobin concentration and oxygen saturation of hemoglobin.

* * * * *